United States Patent [19]
Koch et al.

[11] Patent Number: 5,290,314
[45] Date of Patent: Mar. 1, 1994

[54] FINGER JOINT PROSTHESIS MADE OF METAL

[75] Inventors: Rudolf Koch, Frauenfeld; Yvan Sandoz, Winterthur, both of Switzerland

[73] Assignee: Sulzer Medizinaltechnik AG, Winterhur, Switzerland

[21] Appl. No.: 983,176

[22] Filed: Nov. 30, 1992

[30] Foreign Application Priority Data

Jan. 31, 1992 [CH] Switzerland ............... 00286/92

[51] Int. Cl.$^5$ ............................................. A61F 2/42
[52] U.S. Cl. .................................... 623/21; 623/18
[58] Field of Search ................... 623/21, 16, 18, 20

[56] References Cited

U.S. PATENT DOCUMENTS

| | | |
|---|---|---|
| 3,816,854 | 6/1974 | Schlein . |
| 3,990,118 | 11/1976 | Strickland et al. ............ 623/21 |
| 4,011,603 | 3/1977 | Steffee .......................... 623/21 |
| 4,059,854 | 11/1977 | Laure ............................ 623/21 |
| 4,293,963 | 10/1981 | Gold . |
| 5,133,761 | 7/1992 | Krouskop ...................... 623/21 |
| 5,147,386 | 9/1992 | Carignan et al. .............. 623/21 |
| 5,171,284 | 12/1992 | Branemark ..................... 623/21 |

FOREIGN PATENT DOCUMENTS

| | | | |
|---|---|---|---|
| 0049298 | 4/1982 | European Pat. Off. ............ 623/21 |
| 2814752 | 10/1978 | Fed. Rep. of Germany ........ 623/21 |
| 2126097 | 3/1984 | United Kingdom ................. 623/21 |

*Primary Examiner*—David Isabella
*Assistant Examiner*—Debra S. Brittingham
*Attorney, Agent, or Firm*—Townsend and Townsend Khourie and Crew

[57] ABSTRACT

A finger joint prosthesis, made of metal, has a bearing shell (1) attached to a shaft (2) in the metacarpal and a bearing journal (3) attached to a shaft (5) in the phalange. The bearing journal (3) is designed as a barrel (4), which at right angles to its axis (8) in its center comprises a piece (7) connecting it to its shaft (5). The bearing shell (1) is C-shaped and encloses the barrel (4) with clearance to restrict lateral excursion of the phalange shaft (5), whereas an open area formed by the C-shaped shell restricts the flexion at the connecting piece (7). The C-shaped bearing shell (1) can be forced open when the barrel (4) is inserted because its shaft (2) is divided in the longitudinal direction (13) into two halves (14, 15) by a slit-shaped notch (11) so that the shell and the bearing shell can be engaged by moving them radially towards each other.

16 Claims, 2 Drawing Sheets

FINGER JOINT PROSTHESIS MADE OF METAL

BACKGROUND OF THE INVENTION

The invention relates to a finger joint prosthesis made of metal, which consists of a bearing shell, which is attached to a shaft in the metacarpal and which guides a bearing journal that is, attached to a shaft in the phalange. The bearing journal is constructed as a barrel which at right angles to its axis in its center comprises a connecting piece to its shaft.

During their implantation, finger joint prostheses require enormous dexterity of the surgeon, as fingers in the joint region outside the osseous tissue only comprise a few blood vessels, the ligaments required for movement, the nerves required for tactile sense and also surrounding skin. So as not to endanger the supply to the external finger part, the parts outside the osseous tissue should be impaired in their function as little as possible in the proximal direction. At the same time the joint replacement should imitate the natural range of movement as far as possible.

In U.S. Pat. No. 4,293,963 there is described an artificial elbow joint in which a limited mediolateral swivel movement and a bending and stretching movement are achieved, extreme mediolateral swivel movements of the axis of a metal bearing journal being limited by lateral walls at a bearing shell made of polyethylene. The bearing shell is cut back so that the bearing neck can be moved radially in and out. The shown type of bearing can be altered to a finger joint prosthesis, in which case firstly it occupies a large volume and secondly the joint is not secured in the joint capsule in the radial direction.

SUMMARY OF THE INVENTION

The invention offers a remedy to this problem. It is therefore an object of the invention to create a finger joint prosthesis in which the joint journal is secured in the radial direction and which during the operation enables the radial insertion of the joint journal into the bearing shell.

The advantage of the invention is regarded as being that a secured joint is produced with a minimum of parts, which during the operation can be assembled in a flexed position after the attachment of the bearing journal in the phalange. In this way the blood vessels and tissue parts in the region of the joint are not overstressed because by longitudinally cutting through the upper side of the skin they can be laterally moved away from the bone in a bent position.

DESCRIPTION OF THE PREFERRED EMBODIMENTS

Figure 1:
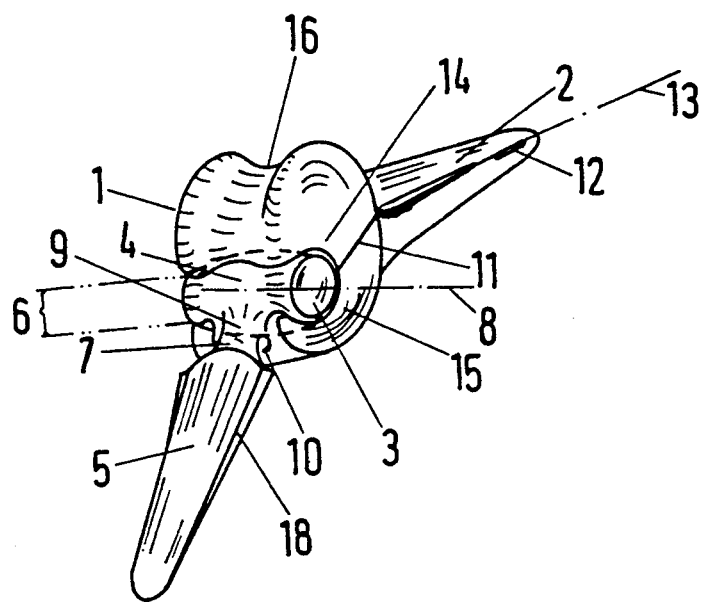
FIG. 1 is a perspective view of a radially assembled finger joint prosthesis in which a C-shaped bearing shell engages a bearing journal.
Figure 2:
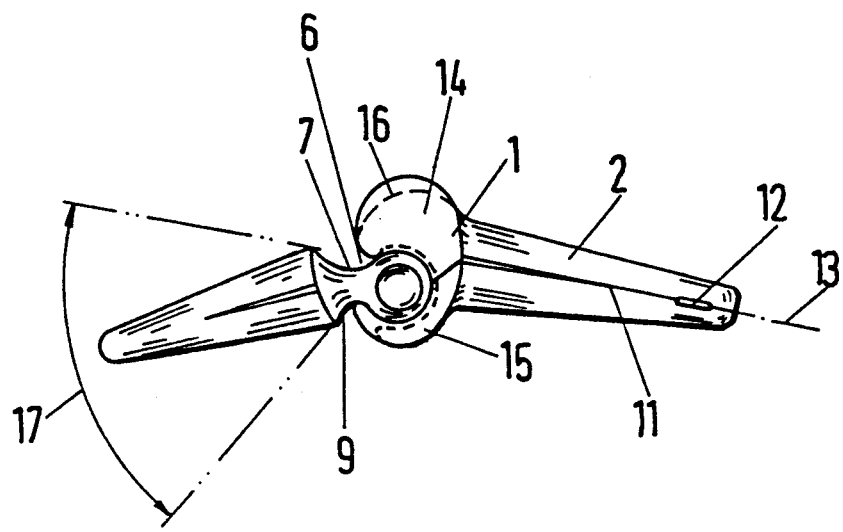
FIG. 2 is a side elevational the view of the finger joint prosthesis in its approximately extended position.

In the figures there is shown a finger joint prosthesis made of metal. It has a bearing shell 1, attached to a shaft 2 in the metacarpal, which guides a bearing journal 3 attached to a shaft 5 in the phalange. The bearing journal 3 is designed as a barrel 4, which at right angles to its axis 8 in its center comprises a connecting piece 7 to its shaft. The bearing shell 1 is C-shaped and encloses the barrel 4 clearance, which limits the lateral excursion of the phalange shaft 5. An opening 6 in the "C" restricts the flexion at the connecting piece 7. The C-shaped bearing shell 1 can be forced open when the barrel 4 is inserted because its shaft 2 is divided into two halves 14, 15 by a slit-shaped notch 11 extending in the longitudinal direction 13 of the shaft.

The bearing journal 3 designed as a barrel 4 is connected by connecting piece 7 to its shaft 5, which tapers conically and comprises a textured surface for attachment to the phalange without cement. The primary attachment is also assisted by longitudinal fins 18, which become embedded in the prepared bone cavity and primarily serve to prevent rotation. After the resection of the phalange and metacarpal (not shown here) the bone cavities are prepared with conical reamers to receive the shafts 2, 5 in their relatively flexed position. Subsequently the bearing journal 3 with its shaft 5 is securely attached in the phalange. The bearing shell 1 also possesses a conically tapering shaft 2 with longitudinal fins 18. It is C-shaped so that it encloses the barrel 4 with clearance. The flex angle 17 of the prosthesis is limited by the extent to which open area 6 of the C-shaped bearing shell extends beyond the connecting piece 7 formed as a neck 9, thereby permitting relatively pivotal movements until the neck engages the upper or lower edge of the bearing shell, the lower edge including a recess 10 which can receive the neck 9. This produces a narrower lateral guide and an enlargement of the flex angle 17. In the longitudinal direction 13 the bearing shell 1 and its associated shaft 2 comprise a slit-shaped notch 11 which starts at the bearing shell 1 and divides the bearing shell 1 and its shaft 2 into two halves 14, 15. This slit is preferably produced with a straight line as generatrix, which is aligned parallel to the axis 8, by, for example, wire electrical discharge machining. The slit ends in a transverse opening 12 just short of the end of shaft 2, so that bearing shell 1 and its shaft 2 remain in one piece but nevertheless can be forced open for the radial insertion of the bearing journal 3. With this design the shaft 2 acts as a curved leaf spring, which determines the position of the two halves 14, 15 with respect to one another and enables their opening against a closing force.

Figure 3:
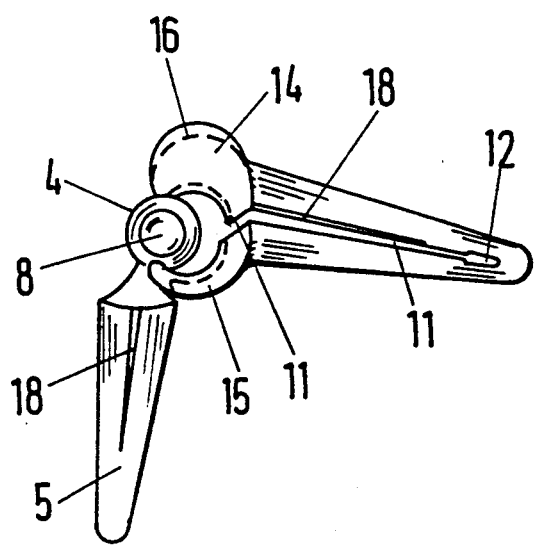
FIG. 3 is an elevational view of a finger joint prosthesis shown in its flexed position with the C-shaped bearing shell forced open during the radial insertion of the bearing journal.

Once the bearing journal 3 is securely attached in the phalange as described above, the bearing shell 1 with its shaft 2 is inserted into a prepared bone cavity in the metacarpal so that it can still be forced open for moving it radially over bearing journal 3. The longitudinal fins on the upper half 14 serve as a preliminary support. They are dimensioned so that with their presence in the prepared bone cavity the lower half 15 can still be sufficiently opened. After the forced opening of the bearing shell 1 and the introduction of the bearing journal 3 as shown in FIG. 3, the bearing shell 1 with its shaft 2 can be driven in the metacarpal so that its structured surface and the longitudinal fins 18 becomes securely attached to the bone without the use of cement. In the fused condition the flex angle 17 is limited by neck 9 and the edges of the C-shaped shell which define open area 6. As the bearing shell 1 is separated, the closing force of the resilient halves 14, 15 and the support in the not completely rigid osseous tissue produce a soft stop. On its upper side the bearing shell 1 has a saddle point 16 for guiding an extensor tendon. The parts outside the shafts 2, 5 not surrounded by osseous tissue comprise a polished surface to prevent the deposit of osseous tissue. The structured surface of the shafts promotes fusion of the structured surface with the surrounding bone. The surfaces of the bearing shell 1, barrel 4 and neck 5 which slide with respect to each other are made from a wear-resistant material combination so as to minimize wear.

In the absence of a closing force between the upper and the lower half of the bearing shell 1 the notch 11 can be designed so that it is a through-notch. In this case it is advantageous to position notch 11 so that the halves 14, 15 of bearing shell 1 and shaft 2, which are completely separated from one another, are immovably pressed together to prevent them from moving in the longitudinal direction 13 and in a direction thereto.

What is claimed is:

1. A finger joint prosthesis made of metal having a bearing shell (1) which is attached to a first shaft (2) adapted to be located in a metacarpal, said bearing shell guiding a bearing journal (3) which is attached to a second shaft (5) adapted to be located in a phalange, the bearing journal (3) having a central axis and at right angles to said central axis comprises a connecting piece (7) to said second shaft (5), characterized in that the bearing shell (1) is C-shaped, engages the bearing journal, restricts a lateral excursion of the bearing shell relative to the bearing journal and limits relative angular flexion between the bearing shell and the bearing journal, and in that the bearing shell (1) can be forced open when moving the journal bearing in a radial direction into the bearing shell by means of a slit-shaped notch extending from the bearing shell (1) and said first shaft (2) and dividing them in a longitudinal direction (13) into two halves (14, 15).

2. A finger joint prosthesis according to claim 1, characterized in that the slit-shaped notch (11) in the shaft (2) ends short of an end of the first shaft remote from the bearing shell so that resulting halves (14, 15) of the bearing shell and the shaft (2) form one piece and form a leaf spring which produces a closing force when the halves (14, 15) are forced open.

3. A finger joint prosthesis according to claim 1, characterized in that the connecting piece comprises a neck (9) which is thinner than the adjacent cross sections of the second shaft (5) and the bearing journal and which, when angularly flexed relative to the bearing shell, enters a recess (10) formed in the bearing shell (1).

4. A finger joint prosthesis according to claim 3, characterized in that surfaces of the bearing shell (1), the bearing journal and the neck (5) sliding on one another are made of a wear-resistant combination of materials.

5. A finger joint prosthesis according to claim 1, characterized in that an upper side the bearing shell (1) comprises a saddle point (16) for guiding an extensor tendon.

6. A finger joint prosthesis according to claim 1, characterized in that the journal bearing, the connecting piece (7) and the bearing shell (1, 14, 15) comprise polished surfaces to prevent the deposit of osseous tissue thereon, and in that the first and second shafts (2, 5) comprise a structured surface to promote their fusion to surrounding bone.

7. A finger joint prosthesis comprising:
   a metacarpal implant including a first stem adapted to be inserted in a cavity formed in a metacarpal bone and carrying a bearing shaft having an axis oriented transversely to the stem; and
   a phalange implant including a second stem adapted to be inserted in a cavity formed in a phalange bone and carrying, on an end of the stem, a generally C-shaped bearing housing adapted to fit over and pivotally engage the bearing shaft and defining edges oriented parallel to the bearing shaft, the phalangeal implant including a slit extending from the bearing housing over a substantial portion of the length of the second shaft dividing the phalangeal implant into first and second, opposing halves;
   whereby the implants can be assembled by temporarily spreading apart the first and second halves of the phalangeal implant and then moving the bearing shaft past the edges in a radial direction into the C-shaped housing and thereafter releasing the halves to fully seat the shaft in the housing; and
   whereby the edges of the C-shaped housing engage the first stem during relative pivotal movements of the implants and thereby limit an angle over which the implants can be pivoted with respect to each other.

8. A finger joint prosthesis according to claim 7 including means for limiting relative movements between the implants in the direction of the bearing shaft axis.

9. A prosthetic finger joint according to claim 8 wherein the movement limiting means includes a cutout formed in at least one of the edges of the C-shaped housing.

10. A prosthetic finger joint according to claim 7 including a neck of a relatively reduced cross-section between and interconnecting the bearing shaft and the first stem.

11. A finger joint prosthesis comprising:
    a first part for implantation in a cavity of a metacarpal bone including a first stem for insertion in the metacarpal cavity, a bearing shaft, and means connecting the shaft to the first stem;
    a second part for implantation in a cavity in a phalange bone including a bearing housing having a concavely shaped bearing surface for pivotally engaging the shaft, the housing extending over an arc of less than 360° to define an open area bounded by first and second edges of the housing extending along the shaft, a second stem attached to the housing, extending transversely away from the housing, ending in a free end and adapted to be inserted in the phalange bone cavity, the second part including a slit extending from the bearing surface of the housing towards the free end of the second stem to define opposing portions of the second part separated by the slit, the slit having a sufficient length to permit spreading of the first and second portions and therewith of the bearing housing edges from a closed position away from each other to enable an insertion of the bearing shaft past the housing edges while said housing edges are spread apart; and
    means for thereafter returning the first and second portions to and maintaining said portions in the closed position so that, thereafter, the shaft and the housing pivotally engage each other.

12. A prosthetic finger joint according to claim 11 wherein the slit extends over the full length of the second stem.

13. A prosthetic finger joint according to claim 11 wherein the slit ends short of the free end of the second stem.

14. A prosthetic finger joint according to claim 11 wherein the means for returning and maintaining comprises means resiliently biasing the first and second portions into the closed position, whereby the bearing shaft is radially inserted into the bearing housing by spreading apart the first and second portions in opposition to a force generated by the biasing means.

15. A prosthetic finger joint according to claim 14 wherein the biasing means is defined by a portion of the second stem proximate the free end.

16. A prosthetic finger joint according to claim 15 wherein the slit ends short of the free end of the second stem so that a section of the second stem between an end of the slit and the free end of the stem defines the biasing means.

* * * * *